(12) United States Patent
Seyr et al.

(10) Patent No.: US 9,271,850 B2
(45) Date of Patent: Mar. 1, 2016

(54) METHOD AND DEVICE FOR CONTROLLING AN ARTIFICIAL ORTHOTIC OR PROSTHETIC JOINT

(75) Inventors: Martin Seyr, Vienna (AT); Christian Plesa, Breitenfurt (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 0 days.

(21) Appl. No.: 13/508,228

(22) PCT Filed: Nov. 12, 2010

(86) PCT No.: PCT/EP2010/006894
§ 371 (c)(1),
(2), (4) Date: May 4, 2012

(87) PCT Pub. No.: WO2011/057793
PCT Pub. Date: May 19, 2011

(65) Prior Publication Data
US 2012/0221120 A1    Aug. 30, 2012

(30) Foreign Application Priority Data
Nov. 13, 2009 (DE) .................. 10 2009 052 894

(51) Int. Cl.
*A61F 2/68* (2006.01)
*A61F 2/64* (2006.01)
*A61F 2/66* (2006.01)
(Continued)

(52) U.S. Cl.
CPC .................. *A61F 2/64* (2013.01); *A61F 2/6607* (2013.01); *A61F 2/68* (2013.01); *A61F 2002/5003* (2013.01); *A61F 2002/5033* (2013.01); *A61F 2002/6818* (2013.01); *A61F 2002/7615* (2013.01); *A61F 2002/7625* (2013.01); *A61F 2002/7635* (2013.01)

(58) Field of Classification Search
CPC ...... A61F 2/68; A61F 2/64; A61F 2002/6818
USPC ....................................................... 623/24, 27
See application file for complete search history.

(56) References Cited

U.S. PATENT DOCUMENTS 5,571,205 A * 11/1996 James .............................. 623/24
6,673,117 B1 * 1/2004 Soss et al. ...................... 623/24
(Continued)

FOREIGN PATENT DOCUMENTS

DE    19859931 A1    7/2000
DE    102006021802 A1    11/2007
(Continued)

OTHER PUBLICATIONS

PCT International Search Report for International Patent Application No. PCT/EP2010/006894, mailed Mar. 14, 2011.

*Primary Examiner* — Bruce E Snow
(74) *Attorney, Agent, or Firm* — Holland & Hart

(57) ABSTRACT

The invention relates to a method and device for controlling an artificial orthotic or prosthetic joint of a lower extremity having a resistance device to which at least one actuator is associated, via which the bending and/or stretching resistance is changed depending on sensor data. During the use of the joint, status information is provided via sensors. During use of the joint, status information is provided via sensors, wherein a cyclic movement different from walking is determined and the resistance is reduced for the duration of the cyclic movement.

16 Claims, 2 Drawing Sheets

(51) Int. Cl.
  *A61F 2/50*  (2006.01)
  *A61F 2/76*  (2006.01)

(56) References Cited

U.S. PATENT DOCUMENTS

| | | |
|---|---|---|
| 6,755,870 B1 | 6/2004 | Biedermann et al. |
| 2006/0135883 A1* | 6/2006 | Jonsson et al. ............... 600/546 |
| 2006/0184280 A1* | 8/2006 | Oddsson et al. .............. 700/245 |
| 2006/0189899 A1* | 8/2006 | Flaherty et al. ............... 600/595 |
| 2008/0114272 A1 | 5/2008 | Herr et al. |
| 2008/0255670 A1 | 10/2008 | Boiten et al. |
| 2010/0228360 A1 | 9/2010 | Pusch et al. |
| 2010/0305716 A1 | 12/2010 | Pusch et al. |
| 2011/0087339 A1 | 4/2011 | Pusch et al. |

FOREIGN PATENT DOCUMENTS

| | | |
|---|---|---|
| DE | 102007053389 A1 | 5/2009 |
| DE | 102008008284 A1 | 8/2009 |
| EP | 0549855 A2 | 7/1993 |
| EP | 1974699 A1 | 10/2008 |
| EP | 1531767 B1 | 12/2008 |
| WO | 2006024876 A2 | 3/2006 |
| WO | 2006088966 A2 | 8/2006 |
| WO | 2007110585 A2 | 10/2007 |

* cited by examiner

METHOD AND DEVICE FOR CONTROLLING AN ARTIFICIAL ORTHOTIC OR PROSTHETIC JOINT

The invention relates to a method and an appliance for controlling an artificial orthotic or prosthetic joint of a lower extremity with a resistance device to which at least one actuator is assigned, via which actuator the flexion and/or extension resistance is changed. depending on sensor data, with status information being made available via sensors during the use of the joint.

Artificial joints, in particular knee joints, for orthoses or prostheses have an upper attachment part and a lower attachment part, which are connected to each other via a joint device. In the case of a knee joint, the upper attachment part has seats for a thigh stump or a thigh rail, whereas the lower attachment part has a lower leg socket or a lower leg rail. In the simplest case, the upper attachment. part is connected. to the lower attachment part pivotably by a monoaxial joint. It is only in exceptional cases that such an arrangement is sufficient to ensure the desired result, for example a supporting action when used in an orthosis, or a natural gait pattern when used in a prosthesis.

To ensure that the different requirements during the various phases of a step or during other actions are satisfied or supported in a way that is as natural as possible, resistance devices are made available that provide a flexion resistance or an extension. resistance. By means of the flexion resistance, it is possible to establish how easily the lower attachment. part can pivot relative to the upper attachment part in the direction of flexion. In a knee joint, therefore, the flexion resistance is used to establish. how easily the lower leg socket or the lower leg rail swings back in relation to the thigh socket or the thigh rail when a force is applied. The extension resistance brakes the forward movement of the lower leg socket or of the lower leg rail and can form an extension limit. stop. In other types of joints, for example the hip joint, or the ankle joint, these observations apply correspondingly to the kinematic relationships.

With adjustable resistance devices, it is possible to adapt the respective flexion and/or extension resistance to the user of the prosthetic or orthotic device or to different walking or movement situations, so as to be able to provide a suitable resistance under changing conditions.

DE 10 2008 008 284 A1 discloses an orthopedic knee joint with an upper part and, arranged picotably on the latter, a lower part which is assigned several sensors, for example a flexion angle sensor, an acceleration sensor, an inclination sensor and/or a force sensor. The extension stop is adjusted according to the sensor data that are determined.

DE 10 2006 021. 802 A1 describes a control system of a passive prosthetic knee joint with adjustable damping in the direction of flexion, for adaptation of a prosthetic device having upper attachment means and a connector element to an artificial foot. The adaptation is made to climbing stairs, wherein a low-moment lifting of the prosthetic foot is detected, and the flexion damping in a lifting phase is lowered to below a level that is suitable for walking on the flat. The flexion damping can be increased depending on the change in the knee angle and depending on the axial force acting on the lower leg.

DP 10 2007 053 389 A1 describes a method and an appliance for controlling an orthopedic joint of a lower extremity with at least one degree of freedom, having an adjustable actuator by which an orthopedic device, comprising upper means of attachment to a limb and an orthopedic joint arranged in an articulated manner distally from the attachment means, is adapted to walking situations that deviate from walking on the flat. Several parameters of the orthopedic device are detected. via sensors, the detected parameters are compared with criteria that have been established on the basis of several parameters and/or parameter profiles and are stored in a computer unit, and a criterion is selected that is suitable on the basis of the detected. parameters or parameter profiles. Flexion resistances, movement ranges, drive forces and/or the profiles thereof are established in accordance with the selected criterion, in order to control special functions that deviate from walking on the flat. A tilt angle of a part of the orthopedic device in space and/or a profile of a change in tilt angle of a part of the orthopedic device can be used as parameter.

The prior art also discloses so-called brake knee joints, in which the flexion and extension resistance is mechanically increased. as the axial load grows. In the simplest case, this is achieved by providing two brake surfaces, which are pressed onto each other by a ground reaction force. Such a design of the brake mechanism cannot be used for modern prosthetic knee joints with controlled resistance devices.

It has proven useful that knee joints offer a high degree of resistance in the stance phase during walking or during standing, wherein the joint is not completely blocked. In a completely extended knee joint, bending of the joint is prevented. by the fact that the force vector lies in front of the joint axis, and the joint is thus forced to the extension limit. stop. As soon as the force vector migrates behind the joint axis, there is a danger of the joint buckling. It is therefore likewise necessary to provide an increased resistance in a position of slight flexion. The fact that the joint, does not completely lock in a position of slight flexion has the advantage that the user of the joint still has possible ways of intervening in the joint movement. For example, should he be standing on stairs and lose his balance, a locked joint would cause him to fall without any control, whereas he is still able to bend a joint with a high flexion resistance by means of the stump force and can thus minimize the consequences of the fall or avoid falling altogether. Likewise, a high degree of damping during standing makes it easier to maneuver the joint in confined spaces or to sit down.

If the joint offers a high degree of resistance, even when it does not completely block, riding a bicycle is impossible or is possible only with great effort, since it is necessary to overcome not just the resistance of the pedals but also the resistance of the joint.

EP 549 855 A1 discloses a method in which a special mode can be adjusted in order to reduce the flexion and/or extension resistance. It is thus possible to ride a bicycle. However, the joint does not then provide any safety during standing, for example when a prosthesis user dismounts or comes to a stop and stands on the leg fitted with the prosthesis. To achieve the safety that is desired and necessary, the device first has to be actively switched back again to the normal mode. This is done, for example, by a sequence of movements that do not normally occur and that indicate that the device has to be switched. For this purpose, it is generally necessary for the user to dismount. from the bicycle, with the result that a potentially unsafe situation arises when switching to the normal mode.

The object of the present invention is to make available a method and an appliance by which it is possible for the resistance device of the joint, in particular of the knee, to be adapted automatically to riding a bicycle, without the need for conscious activation or deactivation of the mode.

This object is achieved by a method and by an appliance according to the present disclosure. Advantageous embodiments and developments of the invention are set forth in the present disclosure.

In the method according to the invention for controlling an artificial orthotic or prosthetic joint of a lower extremity with a resistance device to which at least one actuator is assigned, via which. actuator the flexion and/or extension resistance is changed depending on sensor data, with status information being made available via sensors during the use of the joint, provision is made that a cyclic movement different from walking is determined, and the resistance is reduced for the duration of the cyclic movement. It is thereby possible to automatically detect the presence of a particular movement. status different from walking, for example the movement status of riding a bicycle, in order to then automatically permit adaptation of the resistance to the current movement. By the determination and detection of a cyclic movement, as is represented by riding a bicycle, it is possible to allow a user of the orthosis or prosthesis to ride a bicycle at any time, without the need for conscious and generally awkward activation of a special mode. The reduction in the resistance takes place automatically and is maintained for the duration of the cyclic movement, different from walking. When the cyclic movement is ended, for example when the user of the prosthesis or orthosis comes to a stop or dismounts, it is likewise automatically detected that the cyclic movement has ended, such that the reduction in the resistance is canceled. It is thereby possible to ensure sufficient, safety when the person riding the bicycle comes to a stop or dismounts.

The cyclic movement is preferably determined by an evaluation of kinematic variables, in particular by an evaluation of joint angle data. Depending on the change of the joint angle, it is possible to detect which type of movement. is present, wherein the cyclic movement is preferably determined by an evaluation. of the phase shift between a joint angle and a joint-part inertial angle or two joint-part inertial angles or the change of these angles. An inertial angular velocity is the angular velocity that a joint part exerts with respect to an orientation that is not part of the joint, preferably with respect to the gravitational orientation. Riding a bicycle can therefore be detected on the basis of a cyclic profile of a joint angle, the joint angle velocity, on the basis of the phase shift between the joint angle and an inertial angle of a joint part, or the phase shift between the joint angle velocity and the inertial angular velocity of a joint part. The assessment can be made, for example, on the basis of the length of the vector formed by the components knee angle velocity and inertial angular velocity of the lower leg part.

Moreover, the cyclic movement can be detected on the basis of the time interval between maxima and minima of the joint angle. Since riding a bicycle is a harmonic and very uniform movement, particularly in respect of the knee-joint angle, it is also possible to use the presence or absence of relative maxima or minima in the course of the joint angle in order to detect riding a bicycle. Whereas characteristic relative minima and maxima arise, in a movement cycle when walking on the flat, other characteristic minima and maxima are present with greater frequency when riding a bicycle.

It is likewise generally possible to assume that, when riding a bicycle, the user of the prosthesis or orthosis does not fully extend the knee joint, in order to prevent. blocking of the joint on account of the prosthesis set-up. Therefore, in the absence of complete extension over a plurality of movement cycles, it can be assumed that the movement, involved. in riding a bicycle is being performed, such that, as the movement continues, the resistance is reduced. Therefore, for the resulting maxima of the parameters, that is to say of the joint angle, the joint-angle change or the inertial angle, value ranges are established. within which the determined values must be situated for a cyclic movement to be determined as given.

In addition, a load acting in a lower attachment part, for example the axial force, can be determined, and the resistance can be reduced when the load reaches or is below a threshold value. At least during the upward movement, there are no loads or only very slight. loads, for example axial forces, acting on a lower leg. If, for example, cyclically decreasing axial force profiles are in each case determined for two revolutions, it can be inferred from this that the user is riding a bicycle, such that a reduction of the resistance or of the resistances is indicated.

Since the prosthesis user or orthosis user is always anticipating bending the knee joint when riding a bicycle, in order to avoid a blocking action on account of the mechanical set-up of the joint, a further condition can be made to the effect that a minimal joint, angle must be present for the resistance to be reduced. This ensures that, in an extended knee joint or an almost extended knee joint, an increased resistance is always made available, since it can be inferred from this position that the action of riding a bicycle is ended or interrupted.

For safety reasons, provision is made that the resistance is increased, and the device thus switched. back to a normal mode, if the conditions for reducing the resistance are no longer present. As a further safety means, provision can be made that the flexion resistance is always increased during the extension movement, i.e. the flexion resistance is increased when the pedal is pressed down, since this increase in resistance does not have a negative effect on riding a bicycle, and yet an uncontrolled buckling of the joint of the fitted leg is prevented in the event of the cyclist spontaneously dismounting, coming to a stop or falling off.

In the appliance according to the invention for carrying out the above-described method, with an adjustable resistance device, which is arranged between two mutually articulated components of an artificial orthotic or prosthetic joint of a lower extremity, and with a control device and sensors, which detect status information of the appliance, provision is made that an adjustment device is provided, and that a resistance change called, for by a pattern of movement can be activated and/or deactivated via the adjustment device. In addition to automatic activation, provision is therefore also made of conscious activation of the cycling mode. It is likewise possible for the automatic detection to be switched off when this mode is not needed.

A function of this kind can be the sole control function of a control system. It is likewise possible that it is only part of a functional control system, so as to be available as an auxiliary mode which, during the walking program, reduces the resistance of the joint, at any time when the conditions are met.

An illustrative embodiment of the invention is explained in more detail below with reference to the attached. figures, in which.

Figure 1:
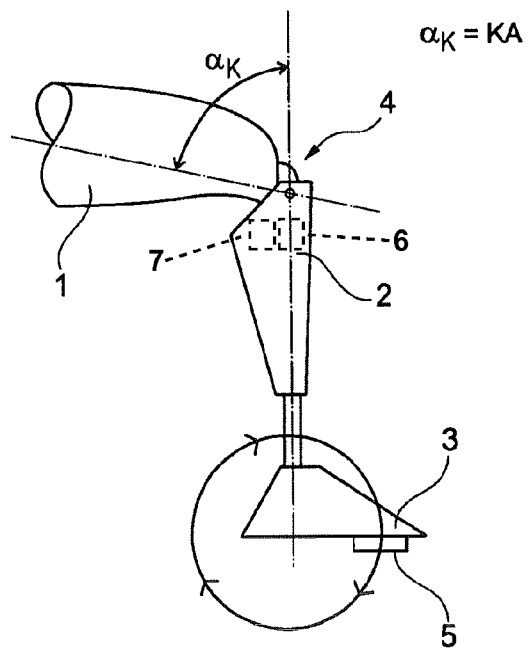
FIG. 1 shows a schematic view of a prosthesis.

In FIG. 1, a prosthesis is shown with a thigh socket 1, with a lower leg part 2 secured in an articulated. manner on the thigh socket 1, and with a prosthetic foot 3. The thigh socket 1 is coupled to the lower leg part 2 via a prosthetic knee joint 4. The thigh of a prosthesis user is received in the thigh socket 1, and resistance devices are provided in the lower leg part 2 so as to be able to adjust the resistance of the pivoting movement between the thigh socket 1 and the lower leg part 2. In the illustrative embodiment shown, the prosthetic foot 3 is positioned on a pedal 5. The contralateral limb (not shown) is not fitted with a prosthesis. A control device is arranged inside the lower leg part 2 and is coupled to sensors. These sensors detect status data of the prosthesis, in particular forces, moments, angular velocities, and angles. On the basis of the sensor data, the control device determines which movement is currently present, such that the correct resistance is automatically set in the resistance device in order to perform the movement correctly and safely.

In the present case, the status of riding a bicycle is intended to be determined. Riding a bicycle is characterized. by a cyclic movement, because the pedal. 5, and therefore also the prosthetic foot 3 placed on the pedal 5, makes a circular movement in a substantially constant direction of rotational movement. This is indicated by the arrow in FIG. 1. The thigh socket 1 performs a pivoting movement about the hip joint, while the lower leg part 2 performs a rotational movement about the joint axis of the prosthetic knee joint 4 and also an upward and downward translation movement.

The knee angle $\alpha_K$ is measured between the longitudinal axis of the lower leg part 2 and the longitudinal axis of the thigh socket 1, the two longitudinal axes intersecting in the prosthetic knee joint 1. Other reference axes are also possible in principle.

Figure 2:
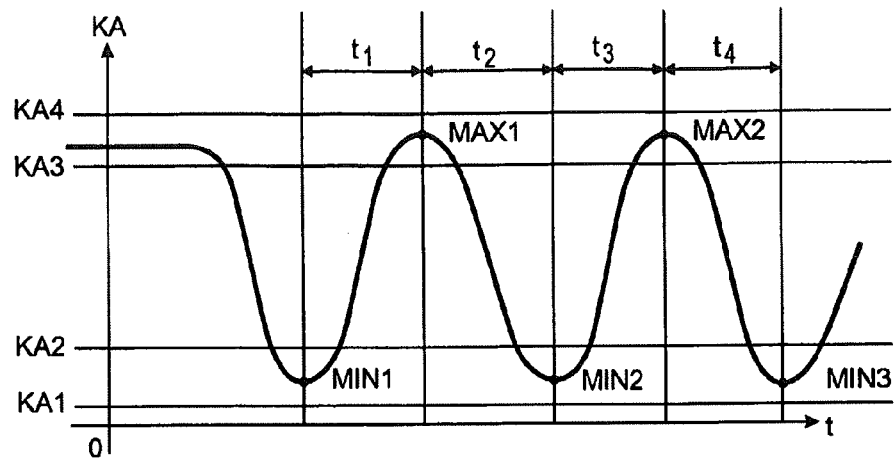
FIG. 2 shows the knee angle profile over time when riding a bicycle.

The profile of the knee angle is plotted over time in FIG. 2 Starting from a position of maximum flexion at the time t=0, the leg fitted with the prosthesis is first of all pushed down. when starting to ride a bicycle, such chat a first knee angle minimum MINI is obtained. Then, over the time the knee angle extends substantially sinusoidally as far as the first knee angle maximum MAX1 and from there, again sinusoidally, to the second knee angle minimum MIN2. This movement pattern and the knee angle profile then continue accordingly, such that an approximately sinusoidal knee angle curve is obtained.

Characteristic of the knee angle profile when riding a bicycle is the fact that the prosthesis is never fully extended, such that the knee angle minimum is located between the not completely extended leg with the knee angle KA1 and the slightly more flexed leg KA2, while the knee angle maximum is located between the values KA3 and KA4, these values being dependent on the saddle height and the pedal length.

If a cyclic profile of the movement is detected in the control device on the basis of the sensor data, such that the minima and maxima within the lower and upper knee angle range have substantially the same time distribution and last for a considerable period, the resistance device is adjusted such that a reduced resistance is provided. Both the flexion resistance and also the extension resistance can be reduced, so as riot to force the cycling prosthesis wearer also to overcome the extension and flexion resistance of the resistance device.

Provision is made chat the first movement cycles are still performed with an increased. resistance, so as to provide increased. safety for the prosthesis wearer. The resistance is reduced only after a certain number of revolutions of the pedal 5. The number of necessary revolutions can be adjusted, for example between two and five revolutions.

In addition to or as an alternative to the evaluation of the cyclic movement on the basis of the knee angle KA, other kinematic variables can be used, for example accelerations or velocities that arise in a recurring pattern when riding a bicycle, for example the special circular movement of the prosthetic foot 3 or the cyclic pivoting movement in connection with the upward and downward movement of the lower leg part 2. These kinematic variables can be used, either as an alternative to or in addition to the knee angle KA, for determining the cyclic movement.

Forces or moments can likewise be used for determining the cyclic movement, for example an axial force that acts in the longitudinal direction of the lower leg part 2 or is applied to the prosthetic foot 3, in order to determine the presence of a bicycling movement. The load, e.g. the axial force, is also provided as a static criterion. if a defined load is present, the action of riding a bicycle is not inferred, but when the load is below a threshold value, it is possible, in conjunction with other data, to infer the action of riding a bicycle, such that a suitably adjusted resistance can be set.

As a safety measure, provision is made that an increase in flexion resistance takes place during the extension movement of the prosthesis. This serves to increase safety, since the increased flexion resistance during the extension movement does not have a negative effect on riding a bicycle but, in the event of the cyclist unintentionally dismounting or suddenly coming to a stop, ensures safety against buckling of the prosthesis.

As a further safety measure, provision is made that the reduced resistance, which can be reduced to zero, is increased to the normal value when the cyclic movements stop, in order in this way to switch automatically to the normal mode in the event of the cyclist coming to a stop and dismounting, that is to say the walking function is made available directly after dismount.

When the leg is in an extended or almost extended. position, the resistance is likewise increased, or not reduced, so as to avoid a situation where no safety is afforded for an extended leg in a standing position in the presence of cyclic loads.

Figure 3:
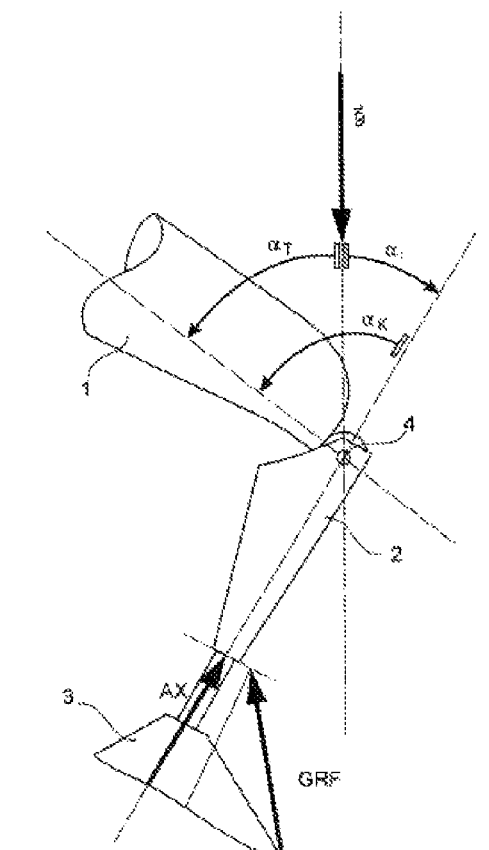
FIG. 3 shows a convention for the angles.

FIG. 3 is a schematic representation of a prosthesis in an angled position. To be able to perform the changes in resistance and provide status determination automatically, provision is made that the inertial angle $\alpha_T$ and/or the knee angle $\alpha_K$ are measured. The inertial angle $\alpha_T$ of the thigh part 1 is measured with respect to the vertical, which is assumed to act in the direction of gravity. In FIG. 3, this is indicated by the gravitational vector g. The reference variable adopted for the inertial angle $\alpha_T$ is the longitudinal axis of the thigh part 1 passing through the pivot axis of the prosthetic knee joint 4. The longitudinal, axis corresponds approximately to the orientation of a natural thigh bone and extends substantially centrally with respect to the thigh part 1, which is generally designed as a thigh socket.

The knee angle $\alpha_T$ lies between the longitudinal extent of the lower leg part 2 and the longitudinal extent of the thigh part 1. Here too, the longitudinal, extent of the lower leg part 2 passes through the joint axis of the prosthetic knee joint 4. The knee angle $\alpha_K$ can be calculated from the inertial angle $\alpha_T$ of the thigh part 1 and the inertial angle $\alpha_i$ of the lower leg part 2, wherein, on the basis of the calculation of the inertial angles $\alpha_T$ and $\alpha_i$ proceeding from the gravitational vector g, a suitable sign rule is introduced, such that the inertial angle $\alpha_T$ of the thigh part 1 is obtained from the difference between the knee angle $\alpha_K$ and the inertial angle $\alpha_i$ of the lower leg part 2.

The ground reaction force GRF or the axial force AX, which acts in the longitudinal direction of the lower leg part 2, is also determined in order to decide, on the basis of the forces present, in which state of movement the prosthesis user is situated.

The invention claimed is:

1. A method for controlling an artificial orthotic or prosthetic joint of a lower extremity, the method comprising:

providing a resistance device, at least one actuator, and sensors;

controlling the resistance device via the actuator to change at least one of a flexion resistance and an extension resistance provided by the resistance device in response to sensor data, with status information being made available via the sensors, the sensors generating the sensor data during use of the joint;

determining with the sensors maxima and minima of at least one of a joint angle and a joint-part inertial angle of the artificial orthotic or prosthetic joint during a time period;

measuring time intervals between the maxima and minima of the at least one of a joint angle and a joint-part angle;

identifying a recurring pattern of the time intervals within the time period;

associating the recurring pattern with a cyclic profile for cycling;

automatically reducing at least one of the flexion resistance and the extension resistance in the joint for a duration of the cyclic profile.

2. The method as claimed in claim 1, wherein the cyclic profile is determined at least in part by an evaluation of kinematic variables.

3. The method as claimed in claim 1, wherein the cyclic profile is determined at least in part by an evaluation of a phase shift between the joint angle and the joint-part inertial angle or two joint-part inertial angles or a change of at least one of the joint angle and the joint-part inertial angle.

4. The method as claimed in claim 1, wherein, for the maximum and minimum, value ranges are established within determined values of the joint angle, the joint-part inertial angle, or a change in joint angle, and is situated for the cyclic profile to be determined.

5. The method as claimed in claim 1, wherein a load acting in a lower attachment part is determined, and the at least one of a flexion resistance and an extension resistance is reduced when the load reaches or is below a threshold value.

6. The method as claimed in claim 1, wherein a minimal joint angle is established that has to be present for the at least one of a flexion resistance and an extension resistance to be reduced.

7. The method as claimed in claim 1, wherein the resistance is increased if conditions for reducing the at least one of a flexion resistance and an extension resistance are no longer present.

8. The method as claimed in claim 1, wherein if the flexion resistance has been reduced, increasing the flexion resistance during an extension movement of the joint.

9. A method for controlling an artificial orthotic or prosthetic joint of a lower extremity, the method comprising:

providing an actuator, a resistance device, and a sensor, the sensor being configured to generate sensor data;

determining with the sensors maxima and minima of at least one of a joint angle and a joint-part inertial angle of the artificial orthotic or prosthetic joint during a time period;

measuring time intervals between the maxima and minima of the at least one of a joint angle and a joint-part inertial angle;

identifying a recurring pattern of the time intervals within the time period;

associating the recurring pattern with a cyclic profile for cycling;

automatically controlling the resistance device with the actuator to reduce at least one of a flexion resistance and an extension resistance for the duration of the cyclic profile.

10. The method as claimed in claim 9, wherein determining the cyclic profile include using an evaluation of kinematic variables.

11. The method as claimed in claim 9, wherein determining the cyclic profile includes using an evaluation of a phase shift between the joint angle and the joint-part inertial angle or two joint-part inertial angles or the change of these the joint angle and the joint-part inertial angle or two joint-part inertial angles.

12. The method as claimed in claim 9, wherein, for the maximum and minimum, value ranges are established within determined values of the joint angle, the joint-part inertial angle, or a change in joint angle for determining the cyclic profile.

13. The method as claimed in claim 9, further comprising determining a load acting in a lower attachment part, and reducing the at least one of the flexion resistance and the extension resistance when the load reaches or is below a threshold value.

14. The method as claimed in claim 9, further comprising establishing a minimal joint angle prior to reducing the at least one of the flexion resistance and the extension resistance.

15. The method as claimed in claim 9, further comprising increasing the at least one of the flexion resistance and the extension resistance if conditions for reducing the at least one of the flexion resistance and the extension resistance are no longer present.

16. The method as claimed in claim 9, wherein if the flexion resistance has been reduced, increasing the flexion resistance during an extension movement of the joint.

* * * * *